United States Patent [19]

Moriya et al.

[11] Patent Number: 5,342,608
[45] Date of Patent: Aug. 30, 1994

[54] GAS CONTAINING CONTRAST AGENT PARTICLES HAVING EXTERNAL MAGNETIC LAYER

[75] Inventors: Tadashi Moriya, Hachioji; Masahiro Seki, Tokyo; Toshiomi Nakamura, Yokohama, all of Japan

[73] Assignee: Nippon Paint Co., Ltd., Osaka, Japan

[21] Appl. No.: 34,744

[22] Filed: Mar. 19, 1993

[30] Foreign Application Priority Data

Mar. 19, 1992 [JP] Japan ................... 4-092425

[51] Int. Cl.$^5$ ................... A61B 8/08; C04B 35/26; A61K 9/16
[52] U.S. Cl. ................... 424/9; 128/662.02; 252/62.56; 424/417; 424/421; 424/490; 424/497; 424/646; 424/648
[58] Field of Search ................... 424/9, 417, 421, 490, 424/497, 646, 648; 128/662.02; 252/62.56

[56] References Cited

U.S. PATENT DOCUMENTS

| | | | |
|---|---|---|---|
| 4,089,800 | 5/1978 | Temple | 252/316 |
| 4,157,323 | 6/1979 | Yen et al. | 260/29.7 M |
| 4,442,843 | 4/1984 | Rasor et al. | 128/660 |
| 4,624,923 | 11/1986 | Margel | 435/176 |
| 4,832,941 | 5/1989 | Berwing et al. | 424/9 |
| 4,844,882 | 7/1989 | Widder et al. | 424/9 |
| 4,871,716 | 10/1989 | Longo et al. | 514/2 |
| 4,911,957 | 3/1990 | Oishi et al. | 427/443.1 |
| 4,957,656 | 9/1990 | Cerny et al. | 252/311 |
| 5,087,438 | 2/1992 | Gordon | 424/9 |
| 5,147,631 | 9/1992 | Glajch et al. | 424/9 |
| 5,160,725 | 11/1992 | Pilgrimm | 424/9 |
| 5,205,287 | 4/1993 | Erbel et al. | 128/632 |
| 5,230,882 | 6/1993 | Unger | 424/9 |

FOREIGN PATENT DOCUMENTS 0416616 3/1991 European Pat. Off. .
0442022A2 8/1991 European Pat. Off. .

*Primary Examiner*—Gary E. Hollinden
*Attorney, Agent, or Firm*—Foley & Lardner

[57] ABSTRACT

Disclosed is a contrast medium for ultrasonic diagnosis, which comprises an aqueous medium and gas-encapsulated particles each having a ferrite magnetic layer on the surface thereof contained in the aqueous medium.

16 Claims, 8 Drawing Sheets

Fig. 14

GAS CONTAINING CONTRAST AGENT PARTICLES HAVING EXTERNAL MAGNETIC LAYER

BACKGROUND OF THE INVENTION

This invention relates to a contrast medium (imaging agent) used for medical ultrasonic diagnosis.

Ultrasonic diagnosis uses acoustic physical phenomena that an ultrasonic wave having a short wavelength travels almost straight in a living body as a slender beam-like sonic wave, and while this beam-like ultrasonic wave travels in living tissues, a part thereof reflects, scatters, decays due to absorption or is influenced by the Doppler effect at the boundary surface of organs or tissues having different acoustic characteristics. Changes of acoustic characteristics are detected by an ultrasonic probe.

In ultrasonic diagnosis of a living body, an ultrasonic contrast medium is used in order to obtain information on cardiac and vascular bloodstreams and a urine stream. This contrast medium is injected parenterally into a circulatory system and moved to an organ to be contrasted, so that it is required that the contrast medium does not cause any damage to a living body, is stable and exhibits good dispersibility in a fluid to be tested.

As an ultrasonic contrast medium which satisfies such requirements, there has been disclosed a dispersion of microspheres having a diameter of 10 μm or less in which fine bubbles are encapsulated in a substance having affinity for an organism obtained by insolubilizing a thermally sensitive protein such as albumin in water in U.S. Pat. No. 4,844,882 and U.S. Pat. No. 4,957,656.

The above contrast medium comprising hollow microspheres in which gas is encapsulated has a large contrast effect, but has problems that the contrast medium cannot be introduced centrally in the vicinity of a site to be observed in a living body, so that an excessive amount of the contrast medium is required, and further, specific gravity of the medium cannot be controlled, so that it cannot be used for observation of a fluid having a slow flow rate such as urine.

SUMMARY OF THE INVENTION

An object of the present invention is to provide a contrast medium for ultrasonic diagnosis, which has a large contrast effect, does not cause any damage to a living body and can move under control in a living body.

Another object of the present invention is to provide a method of ultrasonic diagnosis in which the contrast medium of the present invention is centralized upon a site to be observed by a magnetic field located in the vicinity to the site to be observed.

Still another object of the present invention is to provide a method of ultrasonic diagnosis in which a stream of a fluid of a living body to be tested is visualized in ultrasonic diagnosis by introducing the contrast medium of the present invention to the fluid, and sensitivity and resolution are increased by giving a magnetic gradient from the outside of a body.

The present invention is a contrast medium for ultrasonic diagnosis, which comprises an aqueous medium and gas-encapsulated particles each having a ferrite magnetic layer on the surface thereof which are contained in the aqueous medium. The contrast medium of the present invention can be introduced from the outside of a living body to a site to be observed in a living body without decreasing a contrast effect with a safe magnetic field for a living body, whereby a contrast effect can be obtained by a minimum amount of the contrast medium and the contrast medium can be easily removed to the outside of a living body to prevent side effects.

DESCRIPTION OF THE PREFERRED EMBODIMENTS

In the following, a preferred method for preparing the contrast medium for ultrasonic diagnosis of the present invention is explained.

The particles to be used in the present invention are not particularly limited as long as they have air bubbles internally thereof. The particles to be used in a vascular system preferably have a particle size of 10 μm or less, preferably 5 μm or less, more preferably 1 to 3 μm, but the particles to be used as a tracer in a urinary system may have a particle size of 100 μm or less, preferably 50 μm or less, more preferably 10 to 30 μm.

As the particles, there may be used a hollow particle (or gas encapsulated particles), for example, a hollow glass bead (hereinafter also referred to as a glass balloon particle) and a hollow plastic bead, and also the above insolubilized substance having affinity for an organism may be used. The hollow glass bead may include, for example, Glass Bubbles S60/10000 (diameter: 30 μm), B37/2000 (diameter: 50 μm) and B28/750 (diameter: 80 μm) (trade names, produced by Sumitomo 3M) and HSC110 (diameter: 8 to 12 μm) (trade name, produced by Toshiba Ballotini Co. ). As a fine foamed particle of a natural mineral, Mitsui Perlite (trade name, produced by Mitsui Kinzoku Kogyo Co.) may be mentioned, and also a porous natural mineral obtained by pulverizing pumice or the like may be used. Further, as a hollow polymer particle, there may be mentioned a composite hollow particle described in EP-A-0 416 616.

The ferrite to be attached to the surface of the particle is desirably a ferrite fine particle having high saturated magnetization. A ferrite magnetic layer may be formed on the surface of the particle according to a method disclosed in, for example, U.S. Pat. No. 4,911,957. That is, by adding a ferrous ion, an oxidizer and a pH controller to a deoxidized aqueous solution containing the particles, a ferrite coating layer is formed on the surface of the particle.

The ferrous ion is supplied to the aqueous solution in the form of a salt such as hydrochloride, sulfate and acetate of ferrous iron. When the aqueous solution contains only the ferrous ion as a metal ion, the ferrite coating layer is obtained as a film of a spinel ferrite containing only iron as a metallic element, i.e. magnetite $Fe_3O_4$. In the aqueous solution of the ferrous ion, other transition metal ion $M^{n+}$ may be contained. Such a metal ion may be exemplified by zinc, cobalt, nickel, manganese, copper, vanadium, antimony, lithium, molybdenum, titanium, rubidium, magnesium, aluminum, silicon, chromium, tin, calcium, cadmium and indium. When $M^{n+}$ is a cobalt ion, cobalt ferrite ($Co_xFe_{3-x}O_4$) can be obtained; when $M^{n+}$ is a nickel ion, nickel ferrite ($Ni_xFe_{3-x}O_4$) can be obtained; and when $M^{n+}$s are plural kinds of metal ions, a mixed crystal ferrite can be obtained. These metal ions other than the ferrous ion are incorporated into the aqueous solution in the form of a water-soluble salt, respectively. In the ferrite magnetic layer of the present invention, residual (remanent) magnetism is less when a magnetic field is removed, and it can be dispersed again. The ferrite magnetic layer may be formed continuously or discontinuously on the surface of the particle.

As an example of the oxidizer, there may be mentioned nitrite, nitrate, hydrogen peroxide, an organic peroxide, perchloric acid, a perchlorate or a solution containing dissolved oxygen. It is preferred that the predetermined amounts of an aqueous solution of the oxidizer and an aqueous solution of the metal ion are added dropwise to the above deoxidized aqueous solution as in the titration method in analytical chemistry, and by controlling the amounts of dropwise addition, the thickness of the ferrite film can be controlled easily.

The pH of the aqueous solution may be selected and controlled suitably depending on the kinds of an anion and a metal ion existing in the aqueous solution, but it is preferably in the range of 6 to 11, more preferably 7 to 11. In order to stabilize the pH, a buffer such as ammonium acetate may be added. If necessary, an alkaline solution such as aqueous ammonia may be suitably added during reaction.

As disclosed in Japanese Provisional Patent Publication No. 37019/1991 (which corresponds to EP-A-0 442 022), preferred is a method of forming a ferrite magnetic layer on a particle according to the method described above while controlling a pH-oxidation reduction potential to a suitable range.

The reaction temperature may be in the range of a boiling point of the aqueous solution or lower, preferably in the range of 60° C. to 90° C. The reaction is carried out under substantially deoxidized atmosphere. Under a condition that a large amount of oxygen is present, unnecessary oxidation reaction proceeds undesirably. The reaction is preferably carried out specifically under nitrogen atmosphere. Also, oxygen is removed from the aqueous solution in the same manner, and the resulting deoxidized aqueous solution is used.

The weight ratio of the particle to the ferrous ion or other transition metal ion to be incorporated may vary depending on the kind of a reagent. When the specific gravity of the particle is represented by a, the specific gravity of the ferrite obtained is represented by b and the weight ratio of the particle in the ferrite-coated particle is represented by x %, the specific gravity of the ferrite-coated particle is represented by the following formula:

$$\rho_F = 1/\{x/100a + (1-x/100)/b\}.$$

Preferred is a weight ratio in which $\rho_F$ is 0.1 to 5, preferably 0.9 to 3, more preferably 0.95 to 2, further preferably a specific gravity approximate to that of a body fluid (e.g. blood and urine), i.e. 0.98 to 1.1.

If the specific gravity is less than 0.1, ferrite coating with a sufficient amount cannot be effected, while if it exceeds 5, the particles are precipitated in water or a body fluid, whereby sufficient movability cannot be obtained.

In a preferred preparation method, first, the particles are suspended in deoxidized water, and at that time, if necessary, by adding an additive such as a surfactant, affinity of the particulates for the deoxidized water can be improved. Next, if necessary, by mixing a pH buffer for pH control, the pH is adjusted to a predetermined value. Thereafter, a ferrous ion solution and an oxidizer solution are added to the above suspension. During this addition process, the oxidation reduction potential and the pH of the suspension may be controlled to specific ranges of predetermined values, if necessary. The oxidation reduction potential can be controlled by changing the rate of dropwise addition of the oxidizer solution or the ferrous ion solution to the suspension. The pH can be also controlled by suitably adding an alkaline solution such as aqueous ammonia to the suspension.

The resulting ferrite-coated particles are washed and separated by filtration, centrifugation or dialysis, and may be dried after separation, if necessary.

By classifying the ferrite-coated particles in the suspension, those having a specific gravity approximate to that of a body fluid of a site to be diagnosed can be obtained. The classification may be carried out by a method such as natural or spontaneous precipitation by allowing the suspension to stand or centrifugation. Further, if necessary, an aqueous solvent having a specific gravity being made 1 or more by dissolving an organic salt or a sugar therein; or an organic solvent having a high specific gravity such as carbon tetrachloride may be used. The classification is basically carried out by separating the particles which are precipitated and the particles which are not precipitated. However, if necessary, the classification can be also carried out by collecting an intermediate layer. Thereafter, by further washing the collected particles, the desired ferrite-coated particles can be obtained.

The thus prepared ferrite-coated particles preferably have a thickness of the ferrite film of 0.01 to 0.2 $\mu$m, more preferably 0.01 to 0.05 $\mu$m and a saturation magnetization of preferably 1 to 60 emu/g, more preferably 5 to 20 emu/g.

When the contrast medium of the present invention is used, as in the case of the contrast medium described in U.S. Pat. No. 4,844,882 mentioned above, the contrast medium is injected into a vascular system or a urinary system by an intravenous injection, and can be centralized upon a site to be diagnosed by locating a permanent magnet or an electromagnet in the vicinity of the site to be diagnosed, or giving a magnetic gradient from the outside of a body. Also, the contrast medium may be introduced efficiently to the site to be diagnosed by using a catheter.

Diagnosis using the contrast medium is conducted by reading or measuring a change of an ultrasonic image, a change of echo strength, a change of sound velocity and a change of a decay constant caused by introducing the contrast medium.

When it is difficult to recognize a boundary between a vessel and an organ, the boundary can be recognized by fixing the injected contrast medium at the boundary.

When the contrast medium of the present invention is used for visualizing a fluid having a slow flow rate such as a urine stream in a prostate test, the contrast medium is introduced with a low density (100 grain/cc or less) from a urethra to a bladder by using a catheter, and a stream of urine when a patient passes urine is observed by using ultrasonic waves. A patient having a disorder in passing urine requires several minutes to several ten minutes until urine is passed completely. The contrast medium of the present invention has a specific gravity approximate to that of urine, so that the contrast medium can be dispersed in urine for a long time.

Further, by fixing the contrast medium at the site of a bladder or urethra to be diagnosed, a boundary thereof can be sharpened.

A contrast medium has been used for visualizing an invisible fluid (e.g. a cardiac bloodstream and a bladder), and the contrast medium of the present invention can be used in such a use as a tracer.

As described above, the contrast medium of the present invention comprises particles each having a ferrite magnetic layer on the surface thereof, so that sensitivity and resolution for ultrasonic diagnosis can be improved, and by the effect of magnetism caused by the coated ferrite, it can be introduced to a desired site in a body to be diagnosed. Further, by controlling the thickness of the ferrite film, the specific gravity of the particles can be made approximate to the specific gravity of a body fluid of a site to be diagnosed, whereby the flow rate of the body fluid can be observed.

EXAMPLES

The present invention is described in detail by referring to Preparation examples and Examples.

Preparation Example 1

Preparation of Emulsifying Agent to be Used for Preparing Organic Particles

Into a 2 liter flask equipped with a stirrer, a nitrogen-introducing tube, a temperature-controlling device, a condenser and a decanter were charged 213 g of bishydroxyethyltaurine, 236 g of 1,6-hexanediol, 296 g of phthalic anhydride, 376 g of azelaic acid and 44 g of xylene, and the temperature of the mixture was raised. Water formed by the reaction was removed by azeotropy with xylene. The temperature was raised to 210° C. over about 3 hours after initiation of reflux, and the mixture was reacted by continuous stirring and dehydration until the acid value corresponding to a carboxylic acid became 125. After the temperature of the reaction mixture was dropped to 140° C., 500 g of Cardura E10 (trade name, produced by Shell Co., glycidyl versatate) was added dropwise to the mixture over 30 minutes while maintaining the temperature. Thereafter, the mixture was stirred for 2 hours to obtain an emulsifying agent.

Preparation Example 2

Preparation or Organic Particles

Into a reactor equipped with a stirrer, a condenser, a temperature-controlling device and a nitrogen-introducing tube were charged 50 g of the emulsifying agent obtained in Preparation example 1, 5.0 g of dimethylethanolamine and 508 g of deionized water, and the temperature of the mixture was raised to 80° C. while stirring. Immediately after 80 g of an initiator solution shown below was added to the mixture, dropwise addition of a monomer mixture shown below was started.

| Initiator solution | |
|---|---|
| Azobiscyanovaleric acid | 2 g |
| Deionized water | 100 g |
| Dimethylethanolamine | 1.3 g |
| Monomer mixture | |
| Methyl methacrylate | 100 g |
| n-Butyl acrylate | 50 g |
| Styrene | 200 g |
| Ethylene glycol dimethacrylate | 100 g |

After the dropwise addition was completed over 60 minutes, the remaining 23.3 g of the initiator solution was added to the mixture, and the mixture was stirred for 30 minutes to complete the reaction. The microgel dispersion of the resulting emulsion had a particle size of 0.079 $\mu$m. This emulsion was sprayed and dried to obtain polymer fine particles.

Preparation Example 3

Preparation of Composite Hollow Particles

One gram of 2,2-azobis(2,4-dimethylvaleronitrile) was dissolved in a dispersion in which 15 g of the organic particles obtained in Preparation example 2 was uniformly dispersed in 40 g of styrene, 15 g of methyl methacrylate, 15 g of n-butyl acrylate and 30 g of ethylene glycol dimethacrylate, and the dispersion was added to an aqueous solution of 10 g of Gosenol NH-20 (trade name, produced by Nippon Gosei Kagaku Co.) dissolved in 400 g of deionized water, while stirring at a high rate to prepare a suspension.

The suspension was charged into a 0.5 liter reactor equipped with a stirrer, a condenser, a temperature-controlling device and a nitrogen-introducing tube, and the suspension was heated to 60° C. over 30 minutes under stirring and polymerized over 6 hours at the same temperature.

The resulting dispersion had non-volatile components of 20%. The dispersion was filtered and dried to obtain crosslinkable particles having a mean particle size of 3 $\mu$m. When the section of the particle was observed by an electron microscope, it was found that a hollow was present internally of the particle.

Preparation Example 4

Preparation of Organic Particles 1000 g of deionized water was charged in a reactor equipped with a stirrer, a condenser, a temperature-controlling device and a nitrogen-introducing tube, and the temperature of the deionized water was raised to 80° C. while stirring. Immediately after 205 g of an initiator solution shown below and 50 g of methyl methacrylate were added to the deionized water, dropwise addition of a monomer mixture shown below was started.

| Initiator solution | |
|---|---|
| Ammonium peroxodisulfate | 5 g |
| Deionized water | 200 g |
| Monomer mixture | |
| Methyl methacrylate | 200 g |
| n-Butyl acrylate | 60 g |
| Styrene | 200 g |
| Ethylene glycol dimethacrylate | 40 g |

After the dropwise addition was completed over 120 minutes, the mixture was stirred for 60 minutes to complete the reaction. The microgel dispersion of the resulting emulsion had an average particle size of 0.53 $\mu$m. This emulsion was sprayed and dried to obtain polymer fine particles.

Preparation Example 5

Preparation of Composite Hollow Particles

Two grams of t-butylperoxy-2-ethylhexanate was dissolved in a dispersion in which 10 g of the organic particles obtained in Preparation example 4 was uniformly dispersed in 25 g of styrene, 40 g of methyl methacrylate, 5 g of n-butyl acrylate, 25 g of neopentyl glycol dimethacrylate and 5 g of dimethylaminopropylmethacrylamide, and the dispersion was added to an aqueous solution of 10 g of Gosenol GH-17 (trade name, produced by Nippon Gosei Kagaku Co.) dissolved in 900 g of deionized water, while stirring at a high rate to prepare a suspension.

The suspension was charged into a 1 liter reactor equipped with a stirrer, a condenser, a temperature-controlling device and a nitrogen-introducing tube, and the suspension was heated to 85° C. over 30 minutes under stirring and polymerized over 6 hours at the same temperature.

The resulting dispersion had non-volatile components of 10%. The dispersion was filtered and dried to obtain crosslinkable particles having a mean particle size of 5.3 $\mu$m. When the section of the particle was observed by an electron microscope, it was found that a hollow was present internally of the particle.

Example 1

Preparation of Ferrite-Coated Glass Balloon Particles

Into a reactor was charged 10 g of glass balloon particles Glass Bubbles S60/10000 (trade name, produced by Sumitomo 3M Co., specific gravity: 0.6) having a particle size of about 30 $\mu$m dispersed in 100 g of deoxidized and deionized water. To the dispersion was added 100 g of a deoxidized 4.3 mole/liter ammonium acetate buffer solution, and the mixture was heated to 70° C. while stirring. To the mixture were added dropwise a 1.26 mole/liter ferrous sulfate aqueous solution replaced with $N_2$ gas and a 2.16 mole/liter sodium nitrite solution replaced with $N_2$ gas, both of which had been previously prepared. During the dropwise addition, the temperature was maintained at 70° C., the oxidation-reduction potential was maintained at −480 mV, and the pH was maintained at 7.0 by dropwise addition of aqueous ammonia. After 103 g of the ferrous sulfate solution and 15 g of the sodium nitrite solution were added dropwise over 40 minutes, the reaction was completed. The resulting ferrite-coated glass balloon particles were separated by filtration and washed with water.

Figure 1:
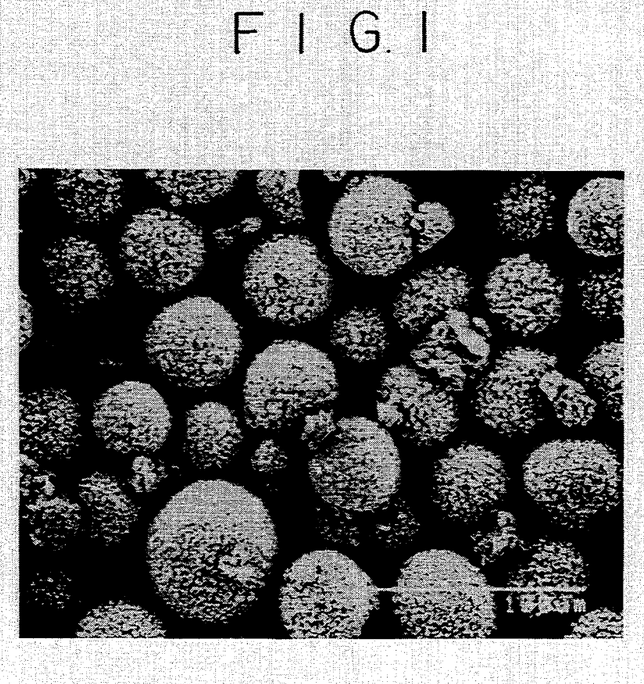
FIG. 1 is a photograph of the ferrite-coated hollow glass beads (hereinafter referred to as the ferrite-coated glass balloon particles) of Example 1 taken by a scanning electron microscope.

The resulting particles were dispersed in 100 g of deionized water, and and the dispersion was left to stand overnight. Then, the floating particles were removed to effect classification. The ferrite-coated glass balloon particles had a specific gravity of 2.2. When the saturated magnetization amount at 10K oersted was measured by using a VSM vibration type magnetism measuring device, it was 42 emu/g. The resulting ferrite-coated glass balloon particles were photographed by a scanning type electron microscope (FIG. 1).

Example 2

Preparation of Ferrite-Coated Glass Balloon Particles

Ferrite-coated glass balloon particles were obtained in the same manner as in Example 1 except for changing the glass balloon particles used in Example 1 to Glass Bubbles B37/2000 (trade name, produced by Sumitomo 3M Co., average particle size: 50 $\mu$m, specific gravity: 0.37), and changing the amount of the ferrous sulfate aqueous solution to 218.3 g. As a result of classification carried out in the same manner as in Example 1, the resulting ferrite-coated glass balloon particles had the specific gravity of 2.0 and the saturated magnetization amount of 26 emu/g.

Example 3

Preparation of Ferrite-Coated Glass Balloon Particles

Ferrite-coated glass balloon particles were obtained in the same manner as in Example 1 except for changing the glass balloon particles used in Example 1 to HSC-110 (trade name, produced by Toshiba Ballotini Co., average particle size: 10 $\mu$m, specific gravity: 1.1), and changing the amount of the ferrous sulfate aqueous solution to 50.7 g. As a result of classification carried out in the same manner as in Example 1, the resulting ferrite-coated glass balloon particles had the specific gravity of 1.6 and the saturated magnetization amount of 17 emu/g.

Example 4

Preparation of Ferrite-Coated Hollow Polymer Particles

Ferrite-coated hollow polymer particles were obtained in the same manner as in Example 1 except for changing the glass balloon particles used in Example 1 to the composite hollow particles obtained in Preparation example 3, and changing the amount of the ferrous sulfate aqueous solution to 94.1 g. As a result of classification carried out in the same manner as in Example 1, the resulting ferrite-coated glass balloon particles had the specific gravity of 1.5 and the saturated magnetization amount of 21 emu/g.

Example 5

Preparation of Ferrite-Coated Hollow Polymer Particles

Ferrite-coated hollow polymer particles were obtained in the same manner as in Example 1 except for changing the glass balloon particles used in Example 1 to the composite hollow particles obtained in Preparation example 5, and changing the amount of the ferrous sulfate aqueous solution to 160.0 g. As a result of classification carried out in the same manner as in Example 1, the resulting ferrite-coated glass balloon particles had the specific gravity of 1.8 and the saturated magnetization amount of 30 emu/g.

Example 6

Preparation of Ferrite-Coated Hollow Polymer Particles

Ferrite-coated organic particles were obtained in the same manner as in Example 1 except for changing the glass balloon particles used in Example 1 to the composite hollow particles obtained in Preparation example 5, and changing the amount of the ferrous sulfate aqueous solution to 41.5 g. Classification was carried out in the same manner as in Example 1, and the classified particles were washed three times in an ethanol aqueous solution adjusted to the specific gravity to 0.95 and allowed to stand for day and night. After removing the separated suspension floated above by decantation, the particles were washed three times by adding a saccharose aqueous solution adjusted to the specific gravity to 1.1 and thereafter allowed to stand for day and night. The separated suspension floated above was removed by decantation, the particles were washed with deionized water. The the resulting particles had the specific gravity of 1.0, the saturated magnetization amount of 11 emu/g and an average particle size of 4.5 μm.

Example 7

Figure 2:
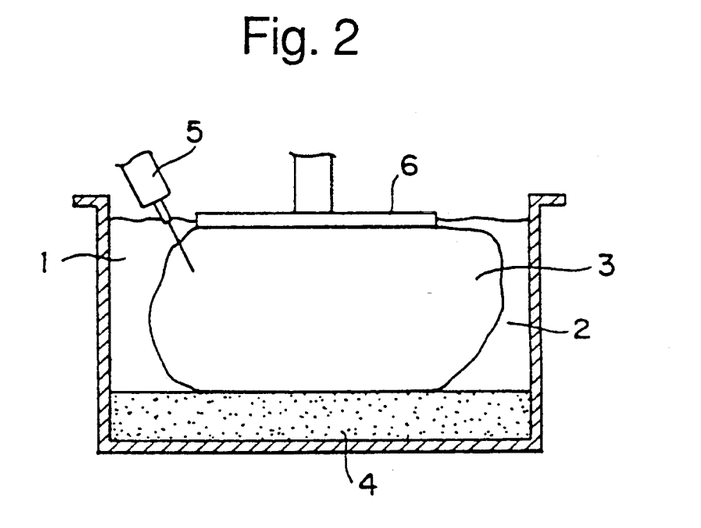
FIG. 2 is a schematic view of a device of a human bladder model.

The respective aqueous solutions containing 1% by weight of the ferrite-coated glass balloon particles or the ferrite-coated hollow polymer particles of Examples 1 to 5 were taken by using syringes, and 1 cc of each solution was injected into a model device of a bladder shown in FIG. 2 (wherein 1 is water, 2 is a rubber ice bag, 3 is deaerated water, 4 is a sponge, 5 is a syringe and 6 is an ultrasonic probe). Immediately after the injection, the model devices were observed by an ultrasonic diagnosis device Model EUB-565 (trade name, manufactured by Hitachi Ltd., equipped with a 3.5 MHz linear scanning probe) for 10 minutes.

Figure 3:
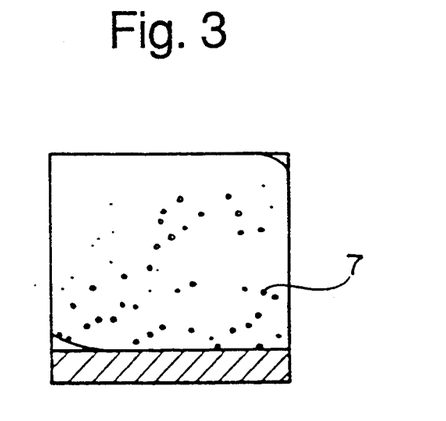
FIG. 3 is a view illustrating a photograph of ultrasonic diagnosis using the ferrite-coated glass balloon particles of Example 1 and measured by the device of a bladder model of FIG. 2.
Figure 4:
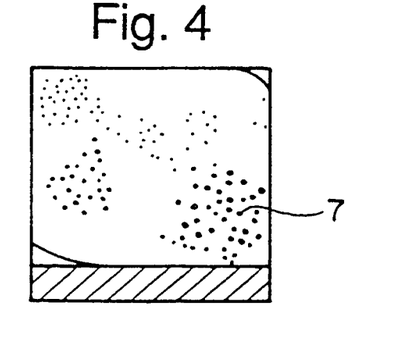
FIG. 4 is a view illustrating a photograph of ultrasonic diagnosis using the ferrite-coated glass balloon particles of Example 2 and measured by the device of a bladder model of FIG. 2.
Figure 5:
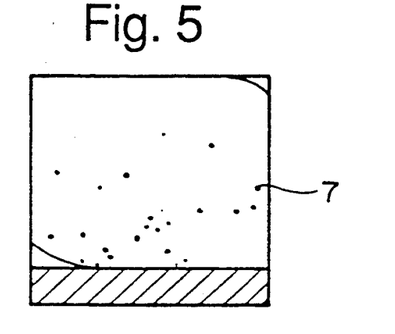
FIG. 5 is a view illustrating a photograph of ultrasonic diagnosis using the ferrite-coated glass balloon particles of Example 3 and measured by the device of a bladder model of FIG. 2.
Figure 6:
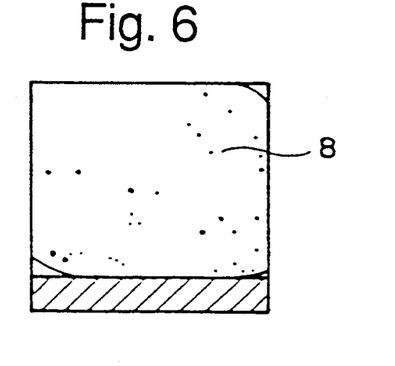
FIG. 6 is a view illustrating a photograph of ultrasonic diagnosis using the ferrite-coated hollow polymer particles of Example 4 and measured by the device of a bladder model of FIG. 2.

FIG. 3, FIG. 4 and FIG. 5 (wherein 7 is a ferrite-coated glass balloon particle) are views illustrating photographs of ultrasonic diagnosis using the ferrite-coated glass balloon particles of Example 1, Example 2 and Example 3, respectively, and FIG. 6 (wherein 8 is a ferrite-coated hollow polymer particle) is a view illustrating a photograph of ultrasonic diagnosis using the ferrite-coated hollow polymer particles of Example 4. In all the photographs, fluid streams could be observed sharply by strong echo caused by resonance scattering.

Example 8

Figure 7:
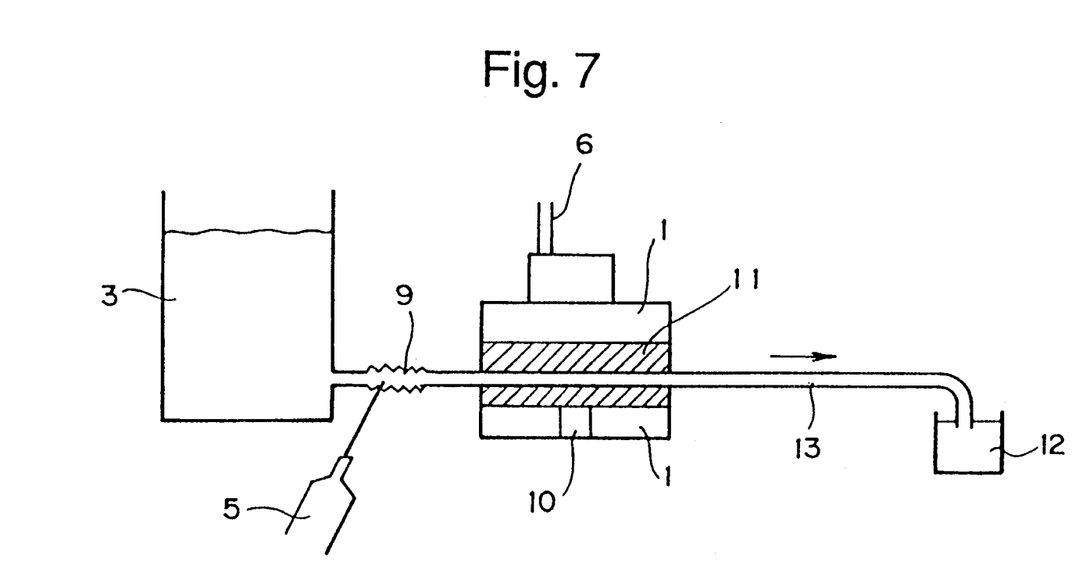
FIG. 7 is a schematic view of a device of a human vascular wall model.

The respective aqueous solutions containing 1% by weight of the ferrite-coated glass balloon particles or the ferrite-coated hollow polymer particles of Examples 1 to 5 were taken by using syringes, and 1 cc of each solution was injected into a device of a human vascular wall model (flow rate: 2 to 3 cm/sec, magnetic flux density: about 140 gauss at 1 cm from the center of magnetic field, magnetic gradient: 20 oersted/mm) shown in FIG. 7 (wherein 1 is water, 3 is deaerated water, 5 is a syringe, 6 is an ultrasonic probe, 9 is a rubber tube, 10 is a permanent magnet, 11 is a perforated konjak jelly, 12 is a flow rate monitor and 13 is a slender pipe). The model devices were observed by an ultrasonic diagnosis device Model EUB-565 (trade name, manufactured by Hitachi Ltd., equipped with a 3.5 MHz linear scanning probe).

Figure 8:
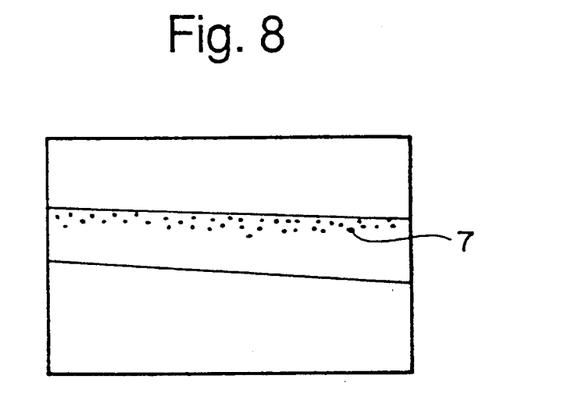
FIG. 8 is a view illustrating a photograph of ultrasonic diagnosis, in which a state when the ferrite-coated glass balloon particles of Example 1 are started to flow in the device of a vascular wall model of FIG. 7 is measured.
Figure 9:
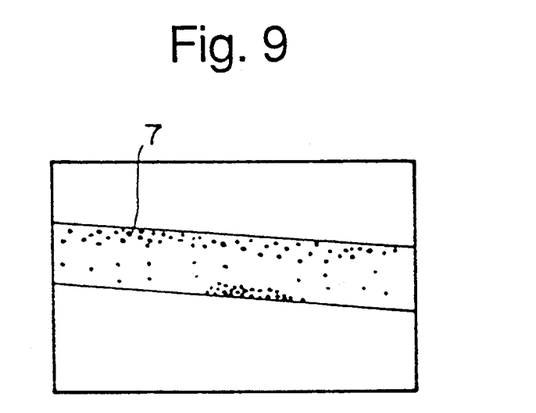
FIG. 9 is a view illustrating a photograph of ultrasonic diagnosis, in which a state one minute after initiation of flowing the ferrite-coated glass balloon particles of Example 1 in the device of a vascular wall model of FIG. 7 is measured.

FIG. 8 (wherein 7 is a ferrite-coated glass balloon particle) is a view illustrating a photograph of ultrasonic diagnosis, in which a state when the ferrite-coated glass balloon particles of Example 1 were started to flow was photographed, and FIG. 9 (wherein 7 is a ferrite-coated glass balloon particle) is a view illustrating a photograph of ultrasonic diagnosis, in which a state one minute after initiation of flowing was photographed. In FIG. 8, the state in which the ferrite-coated glass balloon particles were flowing along the inner wall of the tube could be observed. In FIG. 9, the state in which the ferrite-coated glass balloon particles were gathered at the inner wall surface of the tube could be observed. As to the ferrite-coated particles of Examples 2 to 5, the states similar to those described above could be observed.

Example 9

The ferrite-coated glass balloon particles of Example 1 were filtered by a 0.22 μm filter, and then sterilely washed and replaced with a physiologically saline solution which had been sterilized with high pressure steam to prepare a 10% by weight dispersion in the physiologically saline solution.

A beagle (6 years old, 13 kg, male) was anesthetized by an intramuscular injection of Ketalar (8 mg/kg) at around the root of a hind leg. During the experiment and observation, additional anesthesia was not conducted, and the beagle was not restrained.

Figure 10:
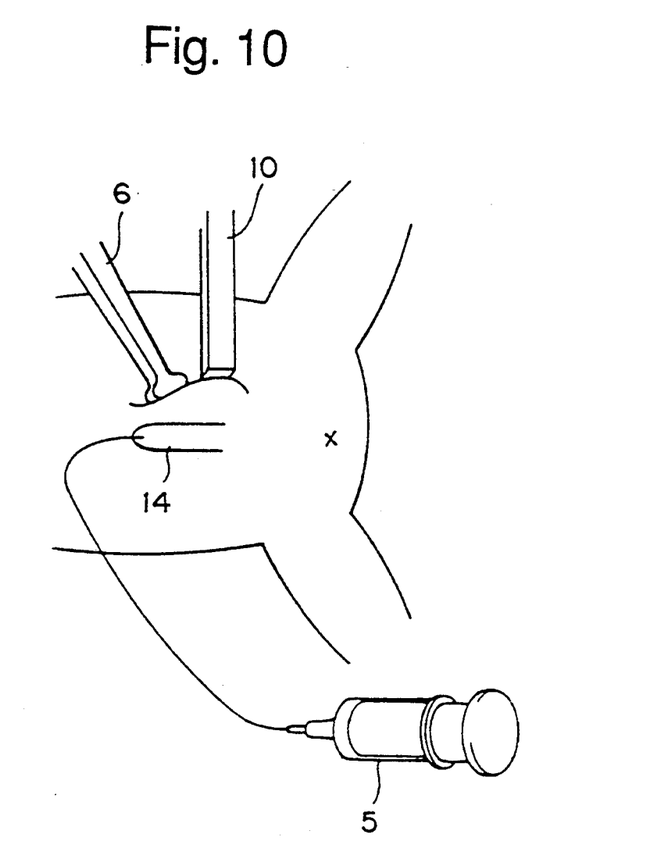
FIG. 10 is a schematic view of measurement of Example 8.
Figure 11:
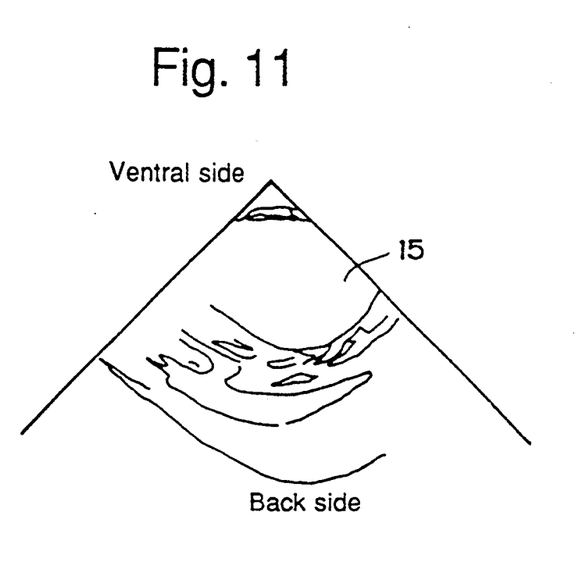
FIG. 11 is a view illustrating a photograph of ultrasonic diagnosis, in which a state of a bladder before injecting the ferrite-coated glass balloon particles of Example 1 thereto in the measurement of Example 8 is measured.
Figure 12:
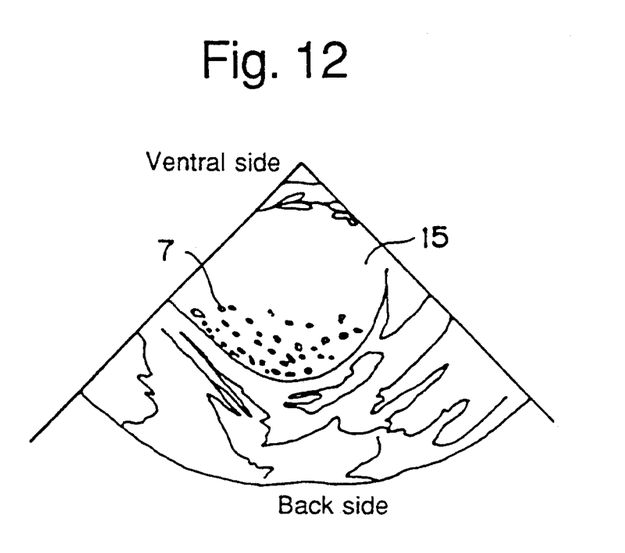
FIG. 12 is a view illustrating a photograph of ultrasonic diagnosis, in which a state of a bladder immediately after injecting the ferrite-coated glass balloon particles of Example 1 thereto in the measurement of Example 8 is measured.
Figure 13:
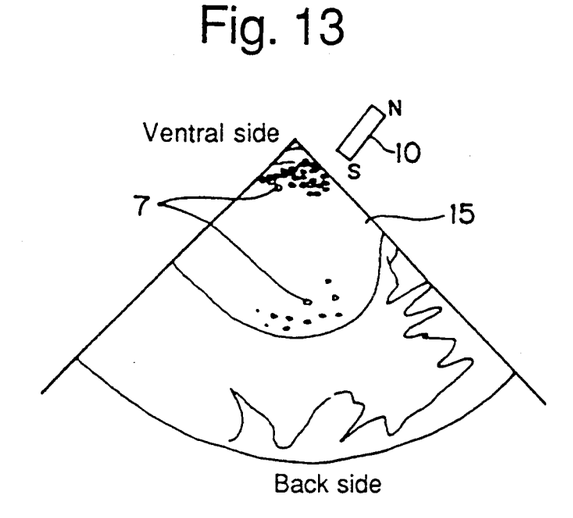
FIG. 13 is a view illustrating a photograph of ultrasonic diagnosis, in which a state of a bladder when the ferrite-coated glass balloon particles of Example 1 are gathered by a magnet is measured.
Figure 14:
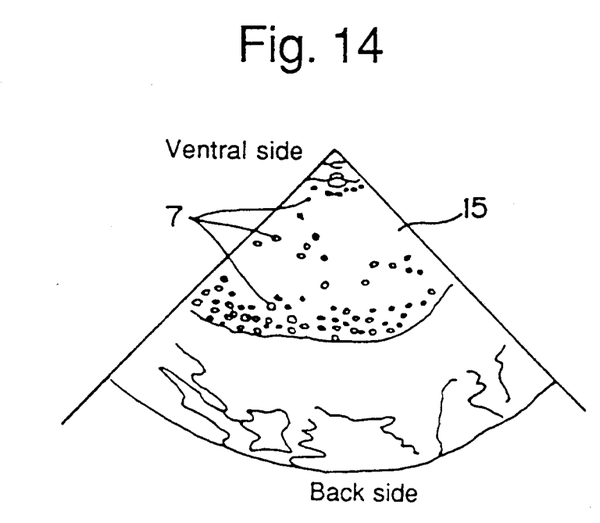
FIG. 14 is a view illustrating a photograph of ultrasonic diagnosis, in which a state of a bladder when a magnet is removed is measured.

A catheter was inserted into the bladder through the urethra. 60 ml of saline, 0.5 ml of the ferrite-coated glass balloon particles suspension described above, and 10 ml of saline were charged. The experimental design was shown in FIG. 10 wherein 5 is a syringe, 6 is an ultrasonic probe, 10 is a permanent magnet and 14 is a penis. The states before and after injection were observed by an ultrasonic diagnosis device Model U-sonic RT5000 (trade name, manufactured by Yokogawa Medical Systems Co., equipped with a 5 MHz probe). FIG. 11 to FIG. 14 are views illustrating photographs of ultrasonic diagnosis showing the following states, respectively. FIG. 11 (wherein 15 is a bladder) shows a state before injecting the dispersion; FIG. 12 (wherein 7 is a ferrite-coated glass balloon particle and 15 is a bladder) shows a state immediately after the injection; FIG. 13 (wherein 7 is a ferrite-coated glass balloon particle, 10 is a permanent magnet and 15 is a bladder) shows a state in which the ferrite-coated glass balloon particles were gathered by a magnet; and FIG. 14 (wherein 7 is a ferrite-coated glass balloon particle and 15 is a bladder) shows a state in which the ferrite-coated glass balloon particles were dispersed again in the bladder by removing the magnet.

After the catheter was removed, black urine containing the ferrite coated glass balloon particles was immediately excreted. After the experiment, the beagle was allowed to have his normal daily activity, and survived beyond 30 days.

We claim:

1. A contrast medium for ultrasonic diagnosis, which comprises an aqueous medium and gas-encapsulated particles each having a ferrite magnetic layer on the surface thereof contained in the aqueous medium.

2. The contrast medium according to claim 1, wherein said particles are hollow particles.

3. The contrast medium according to claim 1, wherein said particles are hollow glass beads.

4. The contrast medium according to claim 1, wherein said particles are hollow plastic beads.

5. The contrast medium according to claim 1, wherein said particles have a specific gravity of 0.3 to 2.

6. The contrast medium according to claim 1, wherein said particles are ferrite-coated hollow particles each having a specific gravity of 0.9 to 3.

7. The contrast medium according to claim 1, wherein the particles have a specific gravity of 0.95 to 2.

8. The contrast medium according to claim 1, wherein the particles have a specific gravity of 0.98 to 1.1.

9. The contrast medium according to claim 1, wherein the particles have a diameter of 200 $\mu$m or less.

10. The contrast medium according to claim 1, wherein the particles have a diameter of 100 $\mu$m or less.

11. The contrast medium according to claim 1, wherein the particles have a diameter of 50 $\mu$m or less.

12. The contrast medium according to claim 11, wherein the particles have a diameter of 10 to 30 $\mu$m.

13. The contrast medium according to claim 1, wherein the particles have a diameter of 10 $\mu$m or less.

14. The contrast medium according to claim 1, wherein the particles have a diameter of 5 $\mu$m or less.

15. The contrast medium according to claim 14, wherein the particles have a diameter of 1 to 3 $\mu$m.

16. A method for ultrasonic diagnosis method which comprises using the contrast medium according to claim 1.

* * * * *